United States Patent [19]

Harmer

[11] 4,187,025

[45] Feb. 5, 1980

[54] DEVICE FOR PRODUCING A LIGHT SIGNAL CORRESPONDING TO THE REFRACTIVE INDEX OF A FLUID

[75] Inventor: Alan L. Harmer, Geneva, Switzerland

[73] Assignee: Battelle Memorial Institute, Geneva, Switzerland

[21] Appl. No.: 919,981

[22] Filed: Jun. 28, 1978

[30] Foreign Application Priority Data

Jul. 1, 1977 [CH] Switzerland ............................ 8105/77

[51] Int. Cl.$^2$ ............................................ G01N 21/46
[52] U.S. Cl. .................................... 356/133; 250/227; 250/577
[58] Field of Search ................ 356/133, 132, 135–137, 356/130; 250/227, 577; 350/96.15

[56] References Cited

U.S. PATENT DOCUMENTS

| | | | |
|---|---|---|---|
| 3,282,149 | 11/1966 | Shaw et al. | 356/130 |
| 3,610,755 | 10/1971 | Wieberger et al. | 350/96.15 |
| 3,969,016 | 7/1976 | Kaiser et al. | 350/96.15 |
| 4,045,668 | 8/1977 | Pitt et al. | 250/227 |
| 4,082,959 | 4/1978 | Nakashima | 250/227 |

FOREIGN PATENT DOCUMENTS

2130037 3/1972 France.

OTHER PUBLICATIONS

American Optical Company Publication Titled "Space Defense", Space Defense Group –Southbridge, Mass.
Journal of the Optical Society of America, vol. 36, No. 1, Jan. 1946, "A Photo-Electric Retractometer" by E. Karrer and R. Orr, pp. 42–46.

*Primary Examiner*—John K. Corbin
*Assistant Examiner*—Bruce Y. Arnold
*Attorney, Agent, or Firm*—Karl F. Ross

[57] ABSTRACT

A device for producing a light signal corresponding to the refractive index of a fluid medium comprises an elongated light-conducting body consisting of an input section and an an output section connected to each other by an intermediate curved section adapted for immersion in said fluid. This curved section is provided with a plurality of curvatures arranged successively and bent alternately in opposite directions, whereby light passing by refraction into said fluid undergoes a notably greater variation, as a function of the refractive index of said fluid medium, than can be obtained with a curved section bent in a simple direction. A light signal is thus provided with a high sensitivity.

11 Claims, 8 Drawing Figures

DEVICE FOR PRODUCING A LIGHT SIGNAL CORRESPONDING TO THE REFRACTIVE INDEX OF A FLUID

FIELD OF THE INVENTION

In many processes, it is required to detect changes of the state of a fluid medium, which may be either discontinuous changes of the state of this fluid (for example presence or absence of liquid) or continuous changes in the physical or chemical properties of this fluid (for example the concentration of a solution or of one of the constituents of a composite fluid, temperature variations of a fluid). This may be used for various applications such as carrying out measurements, control or testing operations and regulation.

BACKGROUND OF THE INVENTION

It has already been proposed, when a correlation exists between the characteristics of the fluid medium and its refractive index, to detect the changes in these characteristics by detecting variations of this refractive index by means of various optical methods. Most of these optical methods are based on exploiting the reflection and refraction phenomena which occur near the critical angle. They essentially consist in transmitting light through a transparent light-conducting structure immersed in the fluid medium, so that light undergoes multiple internal reflections on the walls of the structure. The determination of the intensity of the light thus transmitted by multiple reflections and the sudden variation of this intensity near the critical angle thus permits the refractive index of the fluid to be determined.

To make continuous index measurements there are, for example, devices of the type consisting of a straight transparent rod with an opto-mechanical system at one end for injecting a pencil of light into the rod with a well-defined angle of incidence, and with a photo-electric detector at its other end for measuring the intensity of the light thus transmitted through the rod by multiple internal reflections with a well-defined angle of incidence. When the rod is immersed in the fluid medium to be measured, the angle of incidence of the pencil of light injected into the rod is then made to decrease continuously while observing the transmitted light intensity and the sudden drop in intensity which occurs when the angle of incidence of the multiple relfections exceeds the critical angle with respect to the fluid permits this critical angle to be determined and hence the refractive index of the fluid. Devices of this type however have the major drawback of being extremely complicated, given that they require, among other things, a relatively sophisticated light injection system, since it must ensure both a parallel pencil of incident light by optical means, and a continuous variation of the angle of incidence of this pencil by mechanical means.

Moreover, various known devices for measuring liquid levels are of the type comprising a prism (or cone) placed on the bottom end of a transparent rod inserted into the vessel containing the liquid of which the level is to be determined, indication of this level being obtained by injecting light into the top end of the rod and by observing visually the light reflected by the prism back to the top end (this end is illuminated by reflected light in the absence of liquid at the level of the prism, and becomes dark in the opposite case). Yet devices of this sort have a certain number of drawbacks: firstly the small number of reflections which occur (simple or double reflection) only allows a low light contrast to be obtained, while the light transmission factor remains relatively low; the structure of such devices has moreover proved relatively complicated. But these devices exhibit, above all, the major drawback of being able to function in only two different fluid states due to the fixed incidence of light, so that they are hardly suitable for carrying out continuous index measurements and their use thereby remains limited almost exclusively to the detection of changes of state such as level indication.

In order to remedy the above-mentioned drawbacks, it has further been proposed to use devices consisting of simple transparent rods comprising an intermediate U-shaped curved section adapted for immersion in the liquid to be tested, the refractive index of this fluid being determined by injection of light at one end of the rod and by observing the light transmitted to its other end. In such devices, the curved section of the rod results in the passage by refraction into the liquid of an amount of light which is found to be essentially a function of the refractive index of this liquid, so that the quantity of light transmitted to the other end of the rod constitutes a parameter which is characteristic of this refractive index (a device of this type is described for example in the article "A photo-electric refractometer" by E. Karrer and R. Orr—Journal of the Optical Society of America—Volume 36 No. 1—pages 42 to 46—January 1946). Such devices appear a priori to be particularly advantageous due to their great simplicity and low cost, as well as the fact that they may be used in principle for the detection of both discontinuous and continuous changes in the characteristics of the liquid to be tested. However, these devices exhibit the major drawback of having a very low sensitivity, so that their use as refractometers is quite limited, (because of their inability to be able to detect slight variations of the refractive index of the liquid to be tested), while even their use as simple liquid-level indicators is found to be far from satisfactory (because of the low contrast which can be measured).

It has been proposed more recently to provide different variants of these devices consisting of curved transparent rods, but none of the variants proposed up to the present time has led to a notable improvement of their sensitivity. Thus, for example, it has been proposed to replace the U-shaped rod by a rod with a curvature of at least 360° (U.S. Pat. No. 3,282,149), but this simply serves to linearize the measurement, without notably changing the sensitivity. It has also been proposed, for example, to replace the transparent rod by a curved optical fiber (French Pat. No. 2,130,037) essentially in order to achieve a miniaturization of the equipment, but this mere replacement also has practically no effect on the sensitivity.

OBJECT OF THE INVENTION

The present invention has the object of avoiding the above-mentioned drawbacks by providing a simple device which has a notably increased sensitivity and can detect both discontinuous changes of state of a fluid and continuous variations of various characteristics of this fluid, which are linked to its refractive index.

SUMMARY OF THE INVENTION

To this end, the present invention provides a device for producing a light signal corresponding to the refractive index of a fluid, comprising an elongated light-conducting body consisting of an input section and an output section connected to each other by an intermediate curved section adapted for immersion in said fluid, so that when light is injected into the free end of said input section, the passage of light by refraction into said fluid is a function of the refractive index of said fluid, and the light emerging at the free end of said output section provides a light signal corresponding to the refractive index of said fluid, said device being characterized in that said intermediate curved section comprises a plurality of curvatures arranged successively so as to be alternately bent in opposite directions to one another, whereby said curvatures together provide passage by refraction into said fluid of an amount of light which varies as a function of the refractive index of said fluid, this variation being notably higher than can be obtained with a curved section bent in a single direction to thereby provide said light signal with a high sensitivity.

The present invention also has the object of using such a device for detecting the presence or absence of said fluid, or for measuring a characteristic linked to the refractive index of said fluid.

In the present disclosure, the expressions "elongated light-conducting body" or "light guide" are understood to cover any elongated body capable of conveying light by multiple internal reflections. These expressions are thus understood to cover more particularly light guides consisting of a transparent rod or of an optical fiber (both being formed so as to comprise an intermediate curved section having the desired profile).

It may thus be seen that the essential characteristic of the device according to the invention resides in the use of a light guide comprising an intermediate curved section of several (at least two) alternating curvatures. Such a structure with alternating curvatures provides the major advantage of imparting to the device of the invention a particularly high sensitivity (the degree of sensitivity of such a structure can be determined by the variation of the transmitted light intensity for a given variation of the refractive index of the fluid to be measured), and in any case notably higher than that which can be obtained with a structure with a single curvature (whether it be U-shaped or with a curvature of at least 360°).

The intermediate section with alternating curvatures of the light guide constituting the device according to the present invention may be given various forms, so long as the different curvatures of this intermediate section remain successively arranged in such a manner that each of these curvatures be always bent in a direction opposite to adjacent curvatures. Among the possible forms which may be envisaged, one may use a structure with a double curvature, wherein the last curvature is bent in an opposite direction to the first curvature, or with a triple curvature wherein the middle curvature is bent in an opposite direction to the first and last curvatures, or else a structure having an even greater number of curvatures. In all the above-mentioned structures, the different curvatures may moreover be mutually connected by intermediate straight portions, or on the other hand be directly adjoining (directly connected without being separated from each other by straight portions). In the case of curvatures connected together by means of straight portions, these straight portions will moreover be advantageously chosen so that their length remains relatively small with respect to the dimensions of the curvatures to which they are connected.

In such structures with alternating curvatures as defined above, each of the curvatures may moreover assume any shape, provided it be sufficiently pronounced. As possible forms of curvature, one may thus provide curvatures having a constant radius in the form of an arc of a circle, which may moreover have various lengths such as quarter-circle, half-circle or full circle), or on the other hand curvatures with a variable radius of curvature, which may either increase or decrease progressively. The radius of curvature R of the different curved portions will advantageously be chosen small in relation to the transverse dimensions of the light guide, and to thereby provide a notable effect (the effect due to the curvatures being greater for smaller radii of curvature). This radius of curvature of the different alternating curvatures will preferably be chosen, for a given cylindrical light guide of a radius r, so that the ratio R/r lies between about 3 and 5.

In the case of a light guide consisting of a simple transparent rod, this rod may be made of any appropriate transparent material. Yet this material must be chosen, in the case where the device is used to determine continuous index variations, so as to have a higher index of refraction than that of the measured liquid, whereas it may very well have, in the case where the device is used as a level indicator, any index of refraction, greater or less than that of the measured liquid. As possible transparent materials, one may envisage using plastic materials such as polystyrene ($n=1.59$), polymethylmethacrylate ($n=1.49$), etc. or glasses such as silica (1.458), borosilicate glasses (typical $n=1.5$), lead glasses (typical $n=1.7$), fluoride glasses (typical $n=1.35$), etc.

The size of the cross-section of the light-conducting rod with alternating curvatures according to the invention is of little importance as such, since it is the ratio R/r of the radius of curvature R of the different curvatures to the radius r of the rod which is in fact the determining factor for achieving the desired effect. Thus one may in practice use rods with either a very small cross-section or a relatively large cross-section and then simply adapt in each case each radius of curvature for the selected cross-section of the rod. It is moreover not essential that this cross-section be circular, and one may very well envisage using rods with a square, hexagonal, elliptic cross-section (in such a case the radius of curvature R must be sufficiently small with respect to the cross-sectional rod dimension in the plane of curvature).

In the case of a light guide consisting of an optical fiber, one can in principle carry out the invention with any appropriate type of fiber (these fibers may, moreover, be made of glass-based or plastic-based materials). However, it is particularly advantageous to choose more especially so called step-index fibers. When optical fibers are used, the presence of a cladding around the light-conducting core presents the additional advantage of preventing, in non curved parts of the fiber, any risk of a disturbing influence of a parasitic medium which may possibly be present. As regards the curved portions of these fibers, one may moreover envisage either to strip them completely of their cladding, so as to permit direct contact of the central core with the fluid medium to be tested, or on the other hand to leave them completely protected by their cladding. The results obtained have in fact shown that the presence of a cladding around the curved portions of the fiber does not fundamentally modify the phenomena of light loss by refraction on passage through these curved portions;

the presence of this cladding as a matter of fact leads to only a slight decrease of contrast, the intensity of the transmitted light always remaining characteristic of the surrounding fluid medium to be tested. In this last case, however, (cladded portions), fibers having a cladding of relatively small thickness would preferably be used.

In the present description, the term "angle of incidence of a light ray on a surface" will moreover be used according to its usual definition, namely the angle which this incident light ray makes with respect to the normal to this surface. According to this definition, an increase of obliquity of the incident light ray with respect to the surface is equivalent to a decrease of its angle of incidence.

The definition of two parameters will finally be given which are often used in the following description, in order to explain better the effects provided by the curved section of the device according to the invention, namely, the "coefficient of transmission in air" and the "contrast coefficient" of the device. Thus, in this respect, $I_o$ will be the light intensity injected at the input of the curved light guide, $I_{ta}$ the light intensity transmitted by this guide when the medium surrounding the curved section is air and $I_{tl}$ the light intensity transmitted by this guide when the medium surrounding the curved section is a liquid with an index of refraction n (this liquid may moreover be the liquid to be tested or a reference liquid). One will respectively call "coefficient of transmission in air" the ratio $I_{ta}/I_o$ of the light intensity $I_{ta}$ transmitted by the guide in presence of air to the light intensity $I_o$ injected into the guide (this coefficient permitting to define in a fashion the light losses by refraction in presence of air), and "contrast" or "contrast coefficient" $\Gamma$ the ratio $I_{ta}/I_{tl}$ of the light intensity $I_{ta}$ transmitted in presence of air to the light intensity $I_{tl}$ transmitted in presence of liquid. According to this last definition, the "sensitivity" of the device may also be defined as being represented by the magnitude of the variation of contrast obtained for a predetermined variation of index (sensitivity corresponding to the slope of the curves in the diagram of FIG. 6).

BRIEF DESCRIPTION OF THE DRAWING

The accompanying drawing illustrates, schematically and by way of example, several embodiments as well as variants of the device according to the present invention.

SPECIFIC DESCRIPTION

Figure 1A:
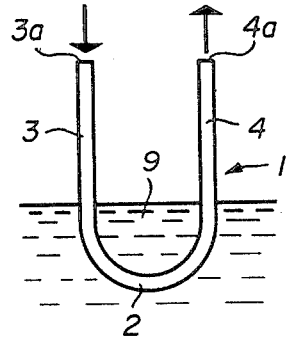
FIGS. 1a and 1b are schematic, longitudinal sectional views illustrating two devices known from the prior art.
Figure 1B:
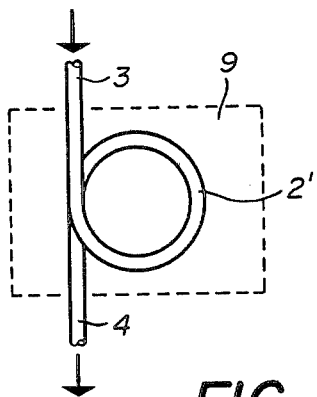

FIGS. 1a and 1b illustrate as an example two devices known from the prior art. These two first illustrations serve to explain the main differences which exist between the known devices and the different embodiments of the device according to the invention which will be described hereafter. The device represented in FIG. 1a comprises a transparent U-shaped rod 1 comprising a curved section 2 of semi-circular form which is prolonged at each of its ends by straight sections 3 and 4. The free end 3a of the straight section 3 serves to inject light into the rod 1, while the free end 4a of the other straight section 4 serves to detect the light transmitted through the rod 1 (injection and output of light schematized by arrows in the drawing). The curved section 2 being immersed in liquid 9 to be tested, the amount of light emerging at the extremity 4a is found to be a function of the index of refraction of the liquid 9. The device represented in FIG. 1b is analogous to that of FIG. 1a, apart from the fact that the curved section 2 of semi-circular form is replaced here by a section 2' which is curved through 360°.

Figure 2:
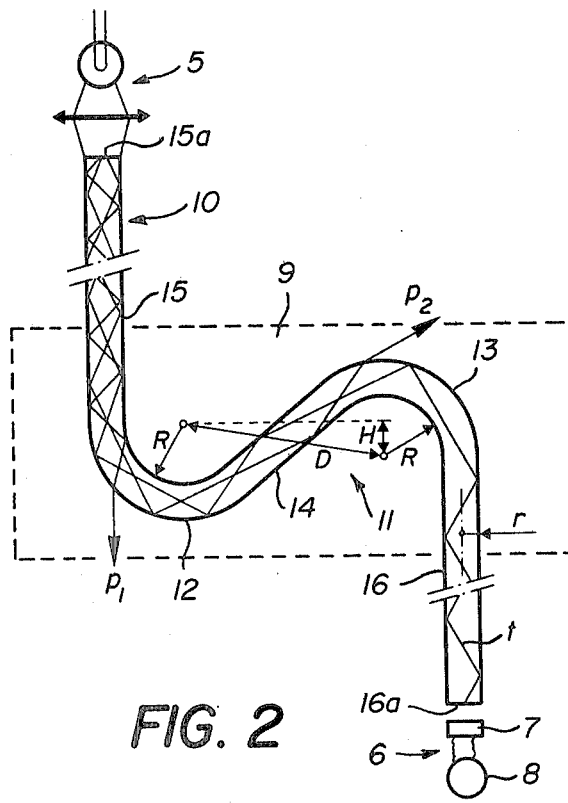
FIG. 2 is a schematic, longitudinal sectional view, illustrating a first embodiment of the device according to the invention.

FIG. 2 illustrates a first embodiment of the device according to the invention, which comprises a light guide consisting of a simple transparent rod provided with two alternating curvatures bent in opposite directions. The device represented in this figure has a rod 10 made of a transparent material, which consists of an intermediate curved, S-shaped section 11 and of two straight sections 15 and 16 extending substantially vertically from each of the ends of this curved section 11. The straight sections 15 and 16 are intended to respectively serve as an input section and an output section for the rod 10. As regards the curved, S-shaped section 11, it consists of two successive curved portions 12 and 13 both in the form of an arc of a circle connected to each other by an intermediate straight portion 14, these two curved portions 12 and 13 being moreover arranged in a substantially symmetrical manner with respect to each other, while being bent in opposite direction to each other. The transparent rod 10 has a circular cross-section of radius r, while the curved portions 12 and 13 have a constant radius of curvature R.

In the vicinity of the plane end-face 15a of the input section 15 there is arranged a light source 5 adapted to inject light into the transparent rod 10, while in the vicinity of the end-face 16a of the output section 16 there is arranged a detection system 6 adapted to determine the light intensity transmitted by the rod 10. For example, this detection system 6 may consist of a photoelectrical detector 7 electrically connected to a measurement and/or display device 8. The curved section of this device is adapted to be immersed in a liquid 9 with a refractive index n, of which one of the characteristics linked to this refractive index is to determined. The transparent material of the rod 10 is chosen so as to have a refractive index $n_1$ greater than the refractive index n of the liquid to be tested.

The geometry of the structure with double curvature which has just been described is essentially controlled by three parameters: the radius of curvature R of each of the curved portions 12 and 13 ( or else the ratio R/r where r is the radius of the rod), the distance D separating the centers of curvaure of each of these curved portions, and their shift H. The radius of curvature R will preferably be chosen relatively small, as a function of r, so as to ensure optimum increase of the contrast and sensitivity of the device. This radius of curvature R will be preferably chosen so that the ratio R/r lies between about 3 and 5. Also for the same reasons, it is moreover of interest to maintain the distance D in the vicinity of the minimum permitted by the radius of curvature (that is, about (2R+2r). Always for the same reasons of contrast and sensitivity, it is finally of interest to choose the shift H to be substantially nil or slightly positive (case represented in FIG. 2).

The operation of the device just described may be explained as follows:

The curved section 11 of this device being immersed in the liquid 9 to be tested, light is injected into the transparent rod 10 by means of the source 5. The light delivered by this source 5 may have any divergence, given that the amount of light effectively trapped by the transparent rod 10 only depends on the "numerical aperture" of this rod and not on the divergence of the incident beam. It is known that the only incident rays which will be trapped within the rod are those which strike its wall at an angle of incidence greater than its critical angle with respect to the surrounding medium (air), the other rays with a smaller angle of incidence being refracted out of the straight section 15. The light so trapped within the transparent rod 10 is then transmitted by multiple internal reflections through the straight section 15, until it arrives in the curved section 11 immersed in the liquid 9 to be tested.

The first curvature 12 of this curved section 11 has the effect of modifying the incidence of the rays which strike its walls, while causing in particular a reduction of the angle of incidence of those rays which come to strike its outer surface (this reduction of the angle of incidence being moreover a function of the magnitude of the curvature), so that these incident rays of which the angle exceeds the critical angle with respect to the surrounding liquid 9 are then forced to pass by refraction into the liquid (behaviour illustrated by the ray $p_1$ in the drawing). For a given curvature, this reduction of the incidence is nevertheless not identical for all the rays which arrive with the same incidence in this curved portion 12, since it depends on the depth at which these rays have been able to penetrate into this curved portion before striking its outer surface, so that only a part of the rays which arrive under the same incidence is liable to pass out of the rod 10 by refraction into the surrounding liquid. This more or less large portion of rays which are liable to be refracted out into the surrounding liquid is evidently a function of the refractive index of this liquid, since the critical angle of total reflection depends on this index. The remaining part of the rays which have not escaped from the rod at this first incidence on the curved portion is then totally reflected into the interior of the rod and transmitted by successive internal reflections to the second curvature 13 (it can be easily shown that it is the first incidence on the curved portion which determines the possibility of passage of the rays into the surrounding medium; a ray totally reflected after this first incidence is then subsequently reflected along the first curvature at constant angles of incidence, equal to that of the first incidence, which no longer allows it to leave the rod up to the next curvature).

The rays totally reflected by the first curvature 12, which tend to be transmitted by multiple reflections along the radially outer surface of this first curvature, then have to arrive in the second curvature 13, due to the inversion of the latter, so that a major part of these rays comes to strike its wall under an extremely low angle of incidence and is thereby forced to pass by refraction into the surrounding medium (behaviour illustrated by the ray $p_2$ in the drawing). This major part of the rays forced to pass by refraction into the surrounding liquid is evidently a function of the refractive index of this liquid, given that the critical angle of total reflection here also depends on this index. The remaining part of the rays which has not escaped from the rod during this first incidence on the second curvature 13 is totally reflected into the interior of the rod (the subsequent incidences in fact occurring at angles equal to that of the first incidence), and hence is transmitted by successive internal reflections up to its other end 16a (behaviour illustrated by the ray t in the drawing).

Consequently, the intensity of the light thus emerging at the other end 16a of the rod, which is substantially equal to the intensity of the light injected into the rod minus the losses due to refraction occurring in the curved portions 12 and 13 (aside from the absorption losses in the rod), is thus likewise a function of the refractive index of the medium surrounding the curved section. This transmitted light intensity hence provides a light signal which is characteristic of and corresponds to the refractive index of the medium surrounding the curved section of the rod.

The light signal thus produced by the device just described nevertheless differs essentially from that produced by the known devices of FIGS. 1a and 1b (although in both cases characteristic of the refractive index of the fluid to to tested) by the fact that it exhibits here a much higher sensitivity, this quite unexpected result being due to the presence of the second curvature 13, bent in the opposite direction to the first curvature 12, which has so to speak an amplifying action on the effects first obtained during passage along this first curvature. This second curvature 13 bent in an opposite direction in fact permits one to multiply the effects obtained during passage of first curvature 12, this being due to the fact that the rays penetrating into this second curvature have already had their path sufficiently modified during their passage in the first curvature so that they must strike the second curvature with a great obliquity (small incident angle), which great obliquity thus obliges the greater part of these rays to leave the rod by refraction at the level of this second curvature (which great obliquity is on the other hand impossible to achieve during penetration into the first curvature, due to the limited "numerical aperture" of the input section 15 of the transparent rod). That the device according to the invention allows a particularly high sensitivity to be achieved (and hence a high contrast) will be clearly demonstrated in the examples further on.

It has been said in the foregoing that it is the first incidence at the entry of the first curvature which determines the refraction losses in this curvature; the rays totally reflected after this first incidence then tend to be transmitted by multiple reflections along the radially outer surface of the curvature under small and constant angles of incidence. It may thus be seen that is unnecessary to increase the length of this curvature by causing it to undergo several turns in the seme direction (case of the known device of FIG. 1b), given that such a measure would only result in reducing the light transmission (due to increased absorption in the transparent material) without in any way increasing the contrast and sensitivity. The only measure found to be effective for notably increasing contrast and sensitivity is that according to the invention, namely, of providing said first curvature followed by at least a second curvature bent in the opposite direction.

The qualitative explanations given above with regard to the effect of the curvatures are in fact only approximate and apply essentially to the meridional rays (i.e. rays intersecting the axis of the light guide), whereas the skew rays which do not intersect this axis nevertheless convey a major part of the light injected into the transparent rod. Yet, it is practically impossible to carry out a theoretical global analysis of the phenomenon, on account of the highly complex behaviour of these skew rays. One could attempt to effect a more complete theoretical approach taking into account the behaviour of these skew rays, by providing a mathematical treatment based on an analysis of the different modes of propagation within the transparent rod. However, such a treatment is already difficult to establish in the case of a single curvature subjected to the penetration of a uniformly distributed radiation, and appears to be very difficult or impossible in the case of a second alternating curvature, due to the non-uniformity of the spatial distribution of the light entering the second curvature (non-uniformity due to the effect of the first curvature which entails a concentration of light energy near the radially outer surface of this curvature).

The qualitative explanations given above, although only approximate, are nevertheless amply corroborated in practice by the different experimental results obtained by measurement of the transmitted light intensity (which takes into account both the skew rays and the meridional rays), as is clearly shown by the examples described further on.

Figure 3:
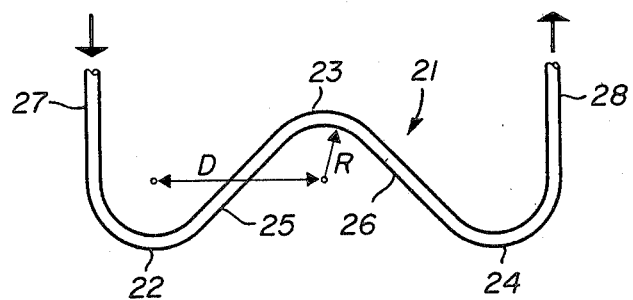
FIG. 3 is a partial longitudinal sectional view illustrating a variant of this first embodiment.

FIG. 3 illustrates a variant of the described embodiment according to FIG. 2, which consists of a transparent rod 21 having three alternating curvatures. The rod 21 in the general shape of a W shown in this figure consists of three curved portions 22, 23 and 24 each in the form of an arc of a circle respectively connected to one another by two intermediate portions 25 and 26 (the curved middle portion 23 being bent in the opposite direction to the outer curvatures 22 and 24), the free ends of the outer curvatues 22 and 24 moreover being prolonged by straight portions 27 and 28.

Figure 4:
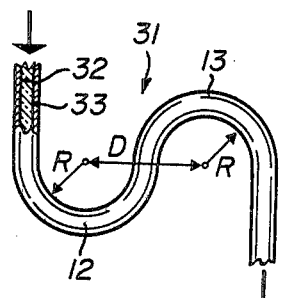
FIG. 4 is a view similar to that of FIG. 3, illustrating a second embodiment.

FIG. 4 illustrates a second embodiment of the device according to the invention, which comprises an optical fiber with a double curvature. This structure is similar to that of FIG. 2, but the transparent rod 10 made of a single material is replaced here by an optical fiber 31, which is composed of a central core 32 surrounded by a cladding of slight thickness 33 along the entire length of the fiber. The geometry of this structure moreover differs from that represented by the FIG. 2 in that the curvatures 12 and 13 are here directly adjoining (i.e. contiguous with no intermediate portion between the curvatures) and are of semicircular form, while the shift H is moreover here chosen equal to zero.

Figure 5:
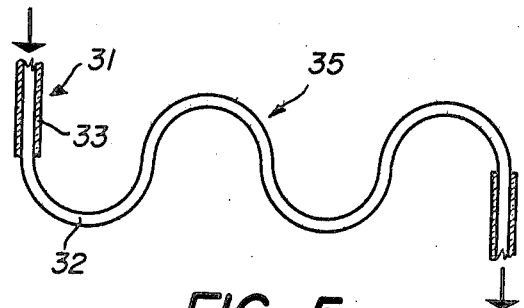
FIG. 5 is a view similar to that of FIG. 4, illustrating a variant of this second embodiment.

FIG. 5 illustrates a variant of the device of FIG. 4, wherein the optical fiber 31 is provided with a curved section 35 comprising four alternating curvatures (instead of two as in FIG. 4), this curved section 35 moreover being completely stripped of the cladding 33 (core 32 laid bare).

EXAMPLE 1

This example serves to establish a comparison between results obtained with the device according to the invention and with devices known from the prior art, so as to show their essential differences.

One uses as starting material a plastic optical fiber PS/PMMA of 1.15 mm external diameter, consisting of a central core of 1.03 mm diameter made of polystyrene (index equal to 1.59) and of a cladding of 60 micron thickness made of polymethylmethacrylate (index equal to 1.49). This fiber is used to make the following structures (all these structures keeping their cladding in the curved portions):

(a) A first structure comprising a simple curvature of 180° (similar geometry to that of FIG. 1a), which presents a radius of curvature R equal to 1.75 mm;

(b) A second structure comprising a single curvature of 360° (similar geometry to that of FIG. 1b), of which the radius of curvature is also equal to 1.75 mm;

(c) A third structure comprising a double alternating curvature (similar geometry to that of FIG. 2), with the following parameters: R equal to 1.75 mm, D equal to 4.65 mm (2R+2r), and H equal to +0.97 mm; and (d) A fourth structure comprising a quadruple alternating curved section (similar geometry to that of FIG. 5), with the following parameters: R equal to 1.75 mm, D equal to 4.65 mm (2R+2r), and H substantially nil.

The above-mentioned structures are made for example by heating the fiber to a temperature between 100° and 200° C., and by forming the fiber thus heated around cylindrical mandrels of appropriate dimensions (having in particular an external radius equal to 1.75 mm).

Light transmission through each of these structures is then measured by means of a source consisting of a 150 W quartz-iodine lamp and a silicon photodiode detector having a spectral response lying between 400 and 950 nm with a peak at 700 nm. A series of measurements is carried out by immersing said structures in liquids of different known refractive indices (ranging from 1.33 to 1.47). The results thus obtained are given in the diagram of FIG. 7, which illustrates the variation of the coefficient of contrast $\Gamma$ as a function of the refractive index n of the liquid in which the different above-mentioned structures are immersed. The curves A and B in FIG. 7 correspond respectively to measurements with the first and second structures known from the prior art, and the curves C and D with the third and fourth structures according to the invention (the curves A and B being practically indistinguishable at the scale of the drawing). This diagram evidently not only clearly illustrates the superiority of the performance (both with regard to the contrast and to the sensitivity) of the structures according to the invention with respect to those known in the prior art, but also more particularly the quite unexpected synergetic effect provided by the alternating curvatures according to the invention: these alternating curvatures indeed allow one to obtain performances which are greatly magnified with respect to the single curvatures used in the prior art, and moreover far greater than a simple doubled or quadrupled performance.

EXAMPLE 2

This example serves to illustrate how light intensity transmitted by the device according to the invention may vary as a function of the magnitude of the curvatures of the light-conducting rod.

As starting material one uses optical fibers (commercially available under the name of CROFON from the Company Dupont de Nemours) of 1 mm external diameter, consisting of a core made of a first plastic material with an index n equal to 1.49 (polymethylmethacrylate) and a cladding made of a second plastic material with an index n equal to 1.39 (thickness of cladding less than 50 microns).

Three optical fiber structures are made with double curvature which are identical to those illustrated in FIG. 4 (namely, a structure having a distance D equal to (2R+2r) and a distance H equal to zero). These curvatures differ from each other in that a different radius of curvature R is chosen in each case, namely respectively 2 mm, 1.75 mm and 1.5 mm (D being then respectively equal to 5 mm, 4.5 mm and 4 mm). Each of these structures is respectively immersed in air and in a reference liquid with a refractive index equal to 1.39 (benzine), and one measures each time the light transmitted through these structures in the same way as before. The resulting measurements allow one to determine, for each of these structures, a contrast coefficient respectively equal to about 8, 18 and 75, as well as a coefficient of transmission in air respectively equal to 55%, 50% and 43%. It may thus be clearly seen that the contrast increases strongly as a function of the degree of curvature, this strong increase with regard to contrast being moreover accompanied by a relatively slight decrease of the coefficient of transmission in air.

The production by the device according to the invention of a light signal which is characteristic of the refractive index of the fluid in which it is immersed may be employed both for detecting discontinuous changes of state of this fluid and for determining different characteristics of this fluid linked to its refractive index (or continuous variations of these characteristics).

In the first of the applications just cited, the device according to the invention may be used particularly advantageously to detect the presence or absence of a fluid at a given place, and more particularly the height or level of the liquid in a given container, the different curvatures constituting the curved section of the light conductor being then disposed at the level to be detected. In this application as a level indicator, the device may be extremely simplified, given that it must only detect two different states: one may thus completely eliminate the system for detecting the transmitted light and replace it by a simple visual observation. The curvature of the curved portions may moreover be advantageously chosen so as to cause minimal losses of light in the absence of liquid, so that the detected end of the light conductor appears darker if the liquid is at the desired level or on the contrary becomes illuminated in the absence of liquid. One may also envisage eliminating the light source permanently mounted at the input end of the light conductor, and replacing it with a simple auxiliary light source (for example a portable lamp such as a flash-light) with which one would light this input end when one desires to verify the level. As regards this liquid-level detection, one may moreover envisage carrying out both a discrete detection (measurement of a single level)and a quasi-continuous detection (measurement of several levels within the same container, for example maximum and minimum levels), and installing a device at each of the levels to be detected.

Figure 7:
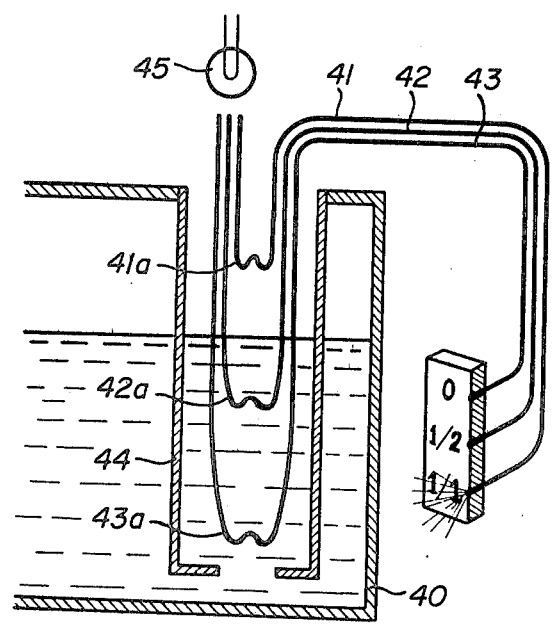
FIG. 7 is a longitudinal sectional view of an apparatus for the detection of a plurality of levels, using several devices according to the invention.

FIG. 7 illustrates an example of an apparatus for measuring three distinct levels within a container 40 (maximum, middle and minimum levels). This apparatus consists of three optical fibers according to the invention, 41, 42 and 43, mounted within a tube 44 immersed in the container 40. These three optical fibers have curved sections 41a, 42a and 43a, in the form of a W arranged at the height of the levels to be measured. In this apparatus, light is injected into the input sections of the fibers by a single common source of light 45, while the indication of level is obtained by simple visual observation of the free ends of the output sections of these fibers. When the container is for example three-quarters full as shown in the drawing, only the output end of the fiber 41 will appear illuminated, while the ends of the two other fibers 42 and 43 will remain dark.

The device according to the invention has multiple applications as a level indicator. One may firstly contemplate using it in the field of automobile (or aeronautic) instrumentation to detect levels such as the levels of a petrol tank, of motor or transmission oil, of brake fluid, of battery electrolyte, of windscreen-washer liquid, etc. The different output ends of the optical fibers used to detect these levels may for example be mounted on the dashboard of the vehicle. One may also consider using such a level indicator in many other fields, such as the storage of liquefied gases (where level measurements are generally difficult to carry out on account of fire hazards, low temperatures and a corrosive environment), storage tanks for chemical products, etc.

The device according to the invention may also be used as a refractometer, in order to measure, either the refractive index of a fluid directly, or other characteristics of this fluid linked to its refractive index, such as the concentration of a solution, proportion of one of the constituents of a composite fluid, temperature of a liquefied fluid, etc. In such an application as a refractometer, the system for detection of the transmitted light may consist of an electric system comprising for example a phototransistor connected to a measurement device, (which may be adapted so as to directly give the value of the characteristic to be measured), or on the other hand by a simple visual system based on the observation of the attenuation of the intensity or colour change (which may possibly be compared with those of a control fiber).

Figure 6:
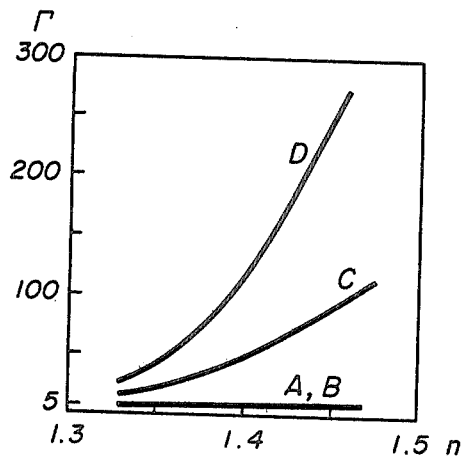
FIG. 6 is a diagram illustrating results obtained with a device according to the invention, as compared with those obtained with known devices of the prior art.

The fields of application of such a refractometer are manifold: chemical industry, medical field, instrumentation in general, automobile or aeronautic instrumentation, etc. In the field of automobile instrumentation, one may consider using this refractometer for applications such as determination of the state of charge of a lead-acid battery or determination of the concentration of an anti-freeze mixture. With regard to this first application to a battery, one can determine the state of the conventional lead-acid battery by measuring the variations of the refractive index of the electrolyte, this index falling from 1.378 at full charge to 1.348 when the battery is discharged; the diagram of FIG. 6 shows that this variation of index would correspond to a variation of the contrast coefficient from about 88 to 35 for the optical fiber corresponding to curve D (respectively a variation of a contrast coefficient from about 35 to 19 for the optical fiber corresponding to the curve C), which can be easily measured visually or electronically. As regards the second application to anti-freeze mixtures, it is moreover known that propylene glycol is increasingly replacing ethylene glycol which is now forbidden in numerous countries due to its high toxicity: the determination of the percentage of ethylene glycol by means of a densitometer can unfortunately no longer be applied to propylene glycol, since its density is very close to that of water, so that the device according to the invention constitutes in this case a particularly advantageous alternative solution.

The device according to the invention has numerous advantages with respect to known level gauges or refractometers: simplicity both in its construction and operation, low cost, high contrast rendering it particularly attractive for use as a level indicator, excellent sensitivity to refractive index changes, making it particularly suitable as a high-performance refractometer.

I claim:

1. A device for producing a light signal corresponding to the refractive index of a fluid, comprising an elongated light-conducting body consisting of an input section and an output section connected to each other by an intermediate curved section adapted for immersion in said fluid, so that when light is injected into the free end of said input section, the passage of light by refraction into said fluid is a function of the refractive index of said fluid and the light emerging at the free end of said output section provides a light signal corresponding to the refractive index of said fluid, said device being characterized in that said intermediate curved section has a profile comprising a plurality of curvatures arranged successively so as to be alternately bent in opposite directions to one another, whereby said curvatures together provide passage by refraction into said fluid of an amount of light which varies as a function of the refractive index of said fluid, this variation being notably higher than can be obtained with a curved section bent in a single direction, to thereby provide said light signal with a high sensitivity.

2. The device according to claim 1, characterized in that said intermediate bent section comprises at least three curvatures with a middle curvature bent in an opposite direction to the two other curvatures.

3. The device according to claim 1, characterized in that said alternately bent curvatures are respectively connected together by intermediate straight portions.

4. The device according to claim 1, characterized in that said curvatures are directly adjoining.

5. The device according to claim 1, characterized in that that the radius of curvature of said curvatures is as small as possible in relation to the transverse directions of said elongated body.

6. The device according to claim 1, characterized in that said elongated light-conducting body consists of a rod made of a transparent material.

7. The device according to claim 1, characterized in that said elongated light-conducting body consists of an optical fiber having a core made of a first transparent material, surrounded by a cladding made of a second transparent material having a refractive index which is less than that of said first transparent material.

8. A device according to claim 7, characterized in that the intermediate curved section of said optical fiber is stripped of said cladding.

9. Use of the device according to claim 1, for detecting the presence or the absence of said fluid.

10. Use of the device according to claim 1, for determining the refractive index of said fluid.

11. Use of the device according to claim 1, for determining another characteristic of said fluid related to its refractive index.

* * * * *